United States Patent
Yanai et al.

(10) Patent No.: US 8,834,345 B2
(45) Date of Patent: Sep. 16, 2014

(54) BACKFLOW DETECTION FOR CENTRIFUGAL BLOOD PUMP

(71) Applicant: Thoratec Corporation, Pleasanton, CA (US)

(72) Inventors: Masamichi Yanai, Ann Arbor, MI (US); Tao Zhang, Ann Arbor, MI (US); Jeffrey G. Houdek, Canton, MI (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 13/742,478

(22) Filed: Jan. 16, 2013

(65) Prior Publication Data

US 2014/0200390 A1 Jul. 17, 2014

(51) Int. Cl.
*A61M 1/10* (2006.01)

(52) U.S. Cl.
CPC .................................. *A61M 1/101* (2013.01)
USPC ............................................................ 600/17

(58) Field of Classification Search
CPC .............. A61M 1/101; A61M 1/1086; A61M 2001/1086
USPC ...................................... 415/900; 600/16, 17
See application file for complete search history.

(56) References Cited

U.S. PATENT DOCUMENTS

| | | | |
|---|---|---|---|
| 5,888,242 A | 3/1999 | Antaki et al. | |
| 6,991,595 B2 | 1/2006 | Burke et al. | |
| 7,033,147 B2 | 4/2006 | Yanai et al. | |
| 7,160,243 B2 | 1/2007 | Medvedev | |
| 7,645,225 B2 | 1/2010 | Medvedev et al. | |
| 8,282,359 B2 * | 10/2012 | Ayre et al. | 417/43 |
| 2011/0313238 A1 | 12/2011 | Reichenbach et al. | |

* cited by examiner

*Primary Examiner* — George Evanisko
(74) *Attorney, Agent, or Firm* — Kilpatrick Townsend & Stockton LLP

(57) ABSTRACT

A centrifugal pump system for a cardiac assist device employs a disc-shaped impeller having an outer circumference adapted to be rotatably driven in a pumping direction. A pump housing has a pumping chamber receiving the impeller, wherein the pumping chamber defines an outlet volute having a separation edge spaced from the outer circumference to provide a limited backflow path coinciding with the pumping direction. A motor drives the impeller in response to a voltage provided to the motor. A current sensor measures current flow within the motor in response to the voltage. A controller estimates a pump flow rate in response to a predetermined relation between the measured current and the pump flow rate, wherein the predetermined relation includes a positive slope from a predetermined backflow rate to a zero pump flow rate.

4 Claims, 5 Drawing Sheets

BACKFLOW DETECTION FOR CENTRIFUGAL BLOOD PUMP

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to circulatory assist devices, and, more specifically, to improved monitoring of the flow rate being output from an implanted pump unit.

Many types of circulatory assist devices are available for either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. One such system is the DuraHeart® LVAS system made by Terumo Heart, Inc., of Ann Arbor, Mich. The DuraHeart® system employs a centrifugal pump with a magnetically levitated impeller to pump blood from the left ventricle to the aorta. An electric motor magnetically coupled to the impeller is driven at a speed appropriate to obtain the desired blood flow through the pump.

A typical cardiac assist system includes a pumping unit, electrical motor (e.g., a brushless DC motor integrated in the pump housing), drive electronics, microprocessor control unit, and an energy source such as rechargeable batteries and/or an AC power conditioning circuit. The system is implanted during a surgical procedure in which a centrifugal pump is placed in the patient's chest. An inflow conduit is pierced into the left ventricle to supply blood to the pump. One end of an outflow conduit is mechanically fitted to the pump outlet and the other end is surgically attached to the patient's aorta by anastomosis. A percutaneous cable connects to the pump, exits the patient through an incision, and connects to the external control unit.

A control system for varying pump speed to achieve a target blood flow based on physiologic conditions is shown in U.S. Pat. No. 7,160,243, issued Jan. 9, 2007, which is incorporated herein by reference in its entirety. A target blood flow rate may be established based on the patient's heart rate so that the physiologic demand is met. The control unit may establish a speed setpoint for the pump motor to achieve the target flow. It is essential to automatically monitor pump performance to ensure that life support functions are maintained. One important performance measurement is the pump flow rate.

The actual blood flow being delivered to the patient by the assist device can be monitored either directly by sensors or indirectly by inferring flow based on motor current and speed. Because of the amount of space that would be required for a flow meter and the desire to maintain minimal size of an implanted device, the blood flow rate is usually estimated indirectly based on the current flowing through the motor and the rotational speed of the motor/impeller. Examples of systems using flow rate estimation include U.S. Pat. No. 7,033, 147 to Yanai et al and U.S. Pat. No. 7,160,243 to Medvedev, both incorporated herein by reference.

A typical centrifugal pump employs a design which optimizes the shapes of the pumping chamber and the impeller rotating within the chamber so that the pump operates with a high efficiency. The pumping chamber has a curved volute shape around the impeller which increases in area as it nears the outlet. The flow into the outlet is substantially tangential to the outer edge of the impeller, and any reverse flow into the pump via the outlet would flow in opposition to the driven direction of the impeller.

The natural pumping action of a patient's heart is pulsatile. Since the assist device is working in conjunction with the beating of the patient's heart, it is subject to this pulsatile flow. As a result, there may be times during the heart cycle in which the assist pump experiences a backflow (i.e., reversal of the flow direction against the impeller rotation). The backflow has been a potential source of inaccuracy in flow rates determined by conventional flow estimation systems. For known pump designs, the motor current exhibits a minimum at a zero flow rate (i.e., as flow decreases toward zero the motor current decreases toward a minimum value which occurs at exactly a zero flow). If the flow decreases further (i.e., reverses to a backflow) then motor current begins to rise because the backflow is working against the impeller. Thus, a backflow condition may be indistinguishable from a small forward flow for estimates based on motor current when the flow is near a zero flow. It would be desirable to be able to unambiguously estimate at least small levels of backflow in order to better assess the pump performance and the physiological state of the patient.

SUMMARY OF THE INVENTION

In one aspect of the invention, a centrifugal pump system comprises a disc-shaped impeller having an outer circumference adapted to be rotatably driven in a pumping direction. A housing has a pumping chamber receiving the impeller, wherein the pumping chamber defines an outlet volute having a separation edge spaced from the outer circumference to provide a limited backflow path coinciding with the pumping direction. A motor drives the impeller in response to a voltage provided to the motor. A current sensor measures current flow within the motor in response to the voltage. A controller estimates a pump flow rate in response to a predetermined relation between the measured current and the pump flow rate, wherein the predetermined relation includes a positive slope from a predetermined backflow rate to a zero pump flow rate.

DETAILED DESCRIPTION OF PREFERRED EMBODIMENTS

Figure 1:
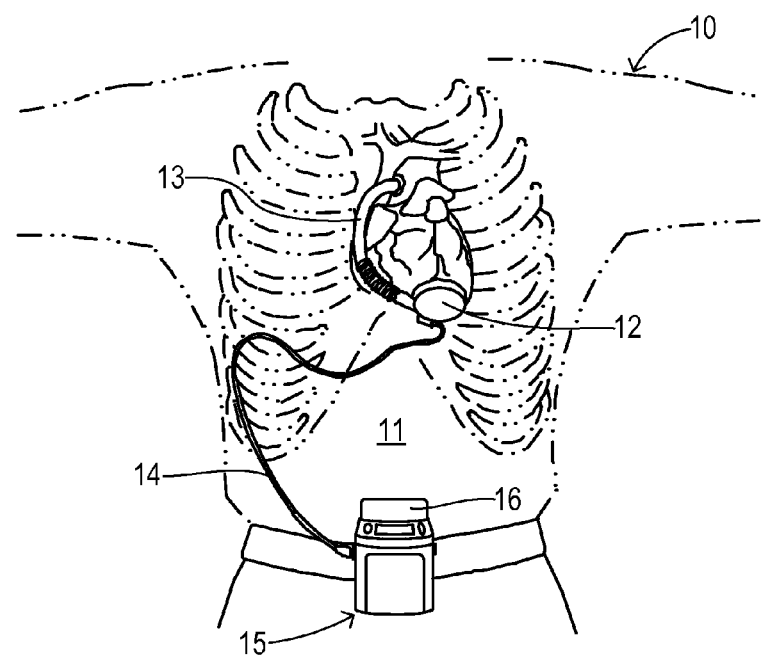
FIG. 1 is a diagram of a circulatory assist system as one example of an implantable pump employing the present invention.

Referring to FIG. 1, a patient 10 is shown in fragmentary front elevational view. Surgically implanted either into the patient's abdominal cavity or pericardium 11 is the pumping unit 12 of a ventricular assist device. An inflow conduit (on the hidden side of unit 12) pierces the heart to convey blood from the patient's left ventricle into pumping unit 12. An outflow conduit 13 conveys blood from pumping unit 12 to the patient's aorta. A percutaneous power cable 14 extends from pumping unit 12 outwardly of the patient's body via an incision to a compact control unit 15 worn by patient 10. Control unit 15 is powered by a main battery pack 16 and/or an external AC power supply and an internal backup battery. Control unit 15 includes a commutator circuit for driving a motor within pumping unit 12. A current sensor is associated with the commutator circuit in order to provide the current measurements on which estimates of the blood flow rate are based.

Figure 2:
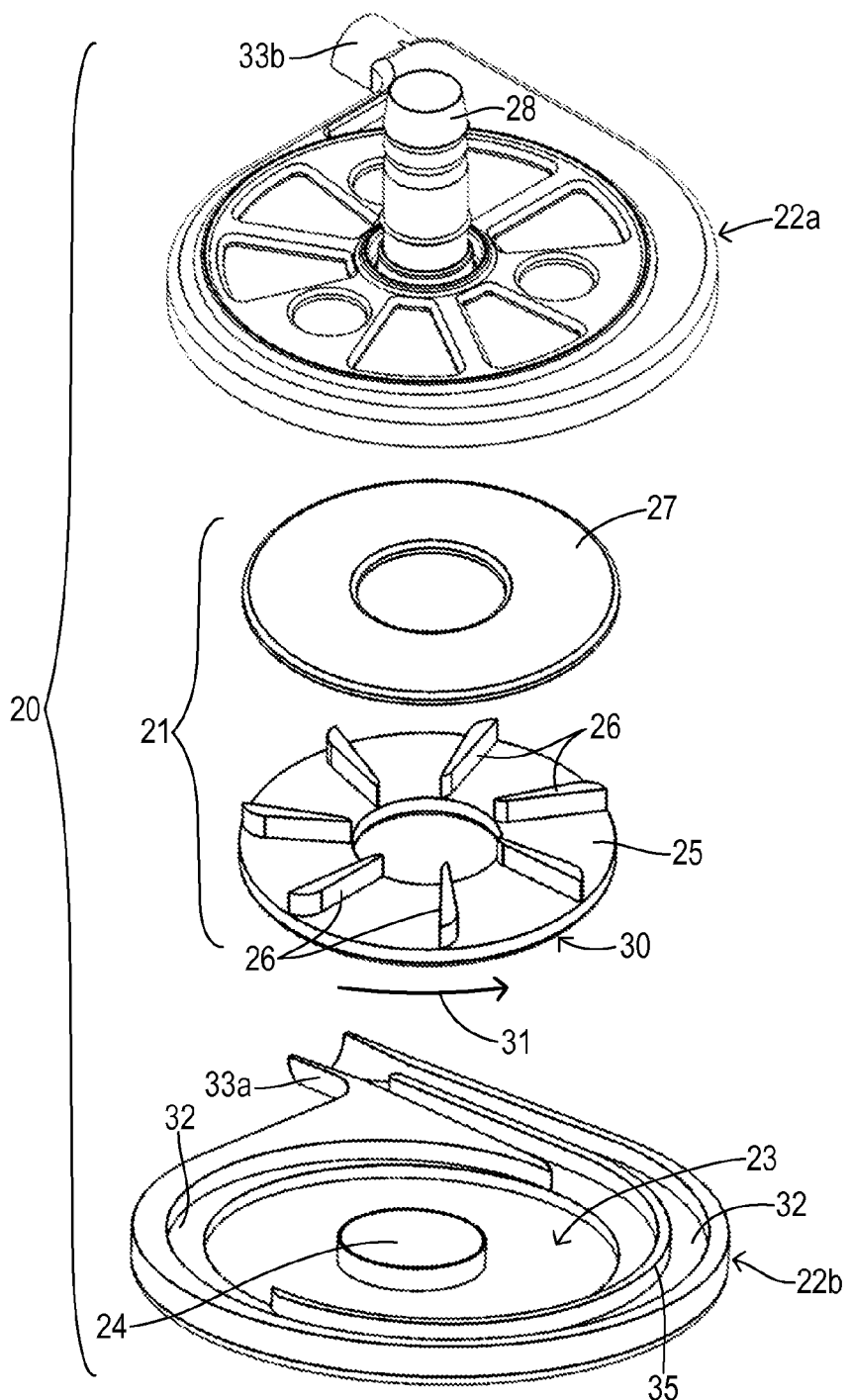
FIG. 2 is an exploded, perspective view of a prior art centrifugal pump.

FIG. 2 shows a centrifugal pump unit 20 having an impeller 21 and a pump housing having upper and lower halves 22a and 22b. Impeller 21 rests within a pumping chamber 23 over a hub 24. Impeller 21 includes a first disc 25 and a second disc 27 sandwiched over a plurality of vanes 26. Second disc 27 may include a plurality of embedded magnet segments for interacting with a levitating magnetic field created by levitation magnets disposed against housing 22a (not shown). First disc 25 also contains embedded magnet segments for magnetically coupling with magnets carried by a motor rotor disposed against housing 22b (not shown). Housing 22a includes an inlet 28 for receiving blood from a patient's ventricle and distributing it to vanes 26. Impeller 21 is preferably circular and has an outer circumferential edge 30. By rotatably driving impeller 21 in a pumping direction 31, the blood received at an inner edge of impeller 21 is carried to outer circumferential 30 and enters a volute region 32 within pumping chamber 23 at an increased pressure. The pressurized blood flows out from an outlet 33 formed by housing features 33a and 33b. A flow-dividing guide wall 35 may be provided within volute region 32 to help stabilize the overall flow and the forces acting on impeller 21.

Figure 3:
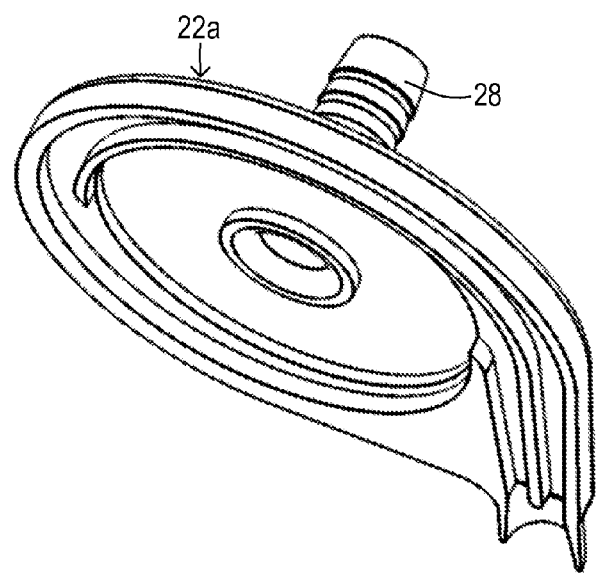
FIG. 3 is a perspective view showing the upper half of the pump housing of FIG. 2.

As shown by FIG. 3, the various features forming the pumping chamber and volute are mirrored inside pump housing 22a.

Figure 4:
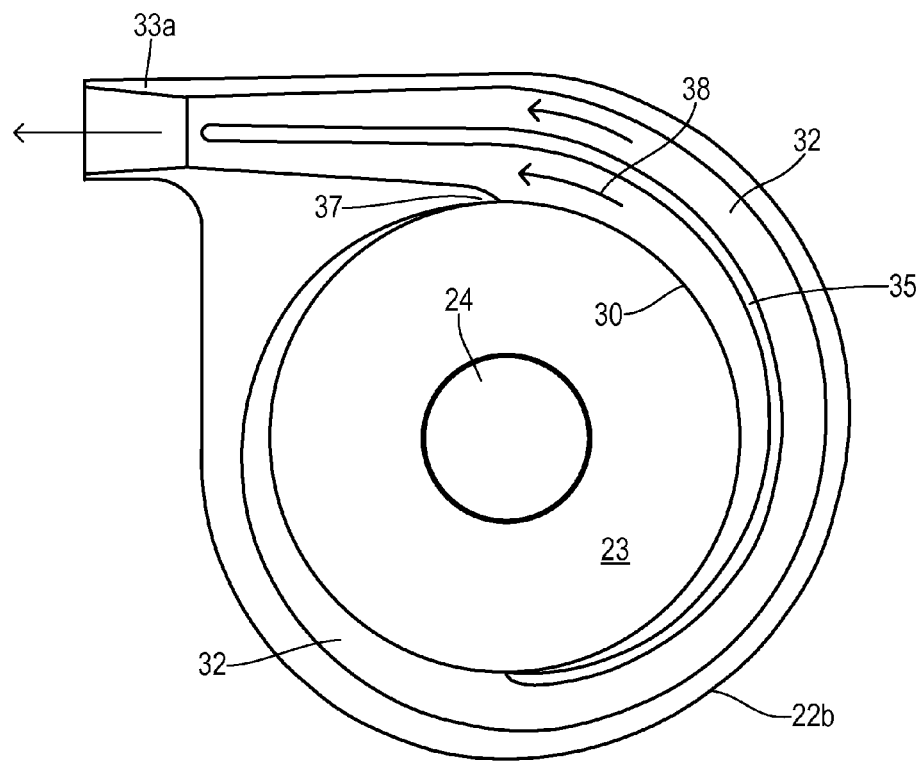
FIG. 4 is a plan view of the lower half of the pump housing of FIG. 2.

As shown more clearly in FIG. 4, volute 32 includes an outwardly spiraling outer edge that controls a flow speed in a desired manner. Housing 22b includes a separation edge 37 in the outlet volute for defining a point where an outlet flow 38 separates from the flow occurring within impeller 21. In this typical prior art design, separation edge 37 is as close as possible to the location of outer circumference 30 of impeller 21 so that all of the flow already in volute 32 is directed into outlet 33.

Figure 5:
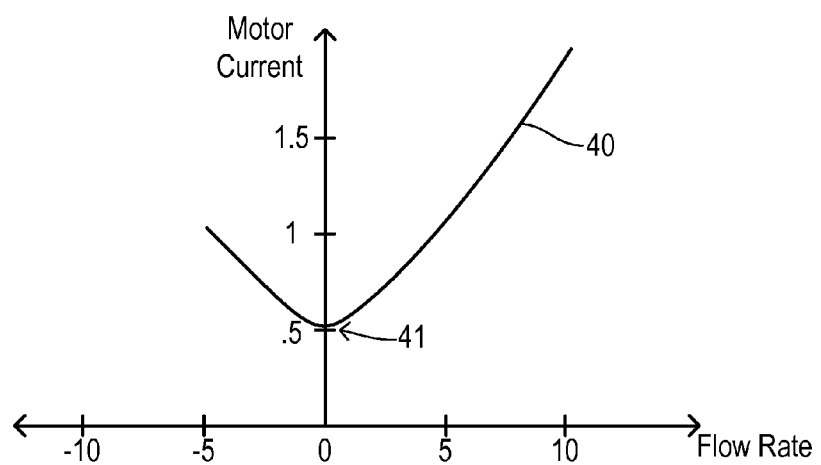
FIG. 5 is a graph showing a relationship between motor current and flow rate for a prior art centrifugal pump.

As a consequence of the volute and separation edge as shown in FIG. 4, the relationship between motor current and flow rate assumes a graphic shape as shown in FIG. 5. For any particular viscosity of the pumped fluid and operating speed of the motor, a relationship 40 can be empirically determined between motor current and pump flow rate. For positive flow rates, relationship 40 has a positive slope such that an increasing motor current corresponds to an increasing flow rate. Relationship 40 has a minima 41 that occurs at a flow rate of zero. For negative flow rates (i.e., a backflow) relationship 40 has a negative slope in which a decreasing flow rate corresponds to an increasing motor current.

Figure 6:
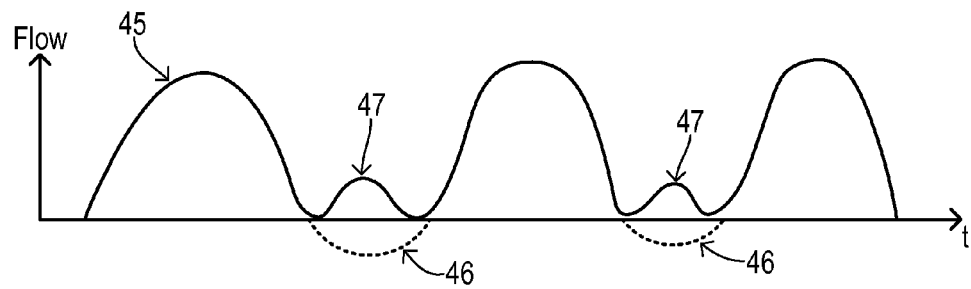
FIG. 6 is a graph of pulsatile flow rate in which a backflow creates an ambiguity in a flow rate estimation.

Due to the ambiguity between motor current and flow rate, conventional estimation of flow rate may exhibit the problem illustrated in FIG. 6. A pulsatile estimated flow rate 45 (solid line) could mistakenly identify an actual backflow rate (shown at dashed lines 46) as being positive flow trajectories shown at 47. Therefore, the overall flow rate over a particular heart cycle can be overestimated.

Figure 7:
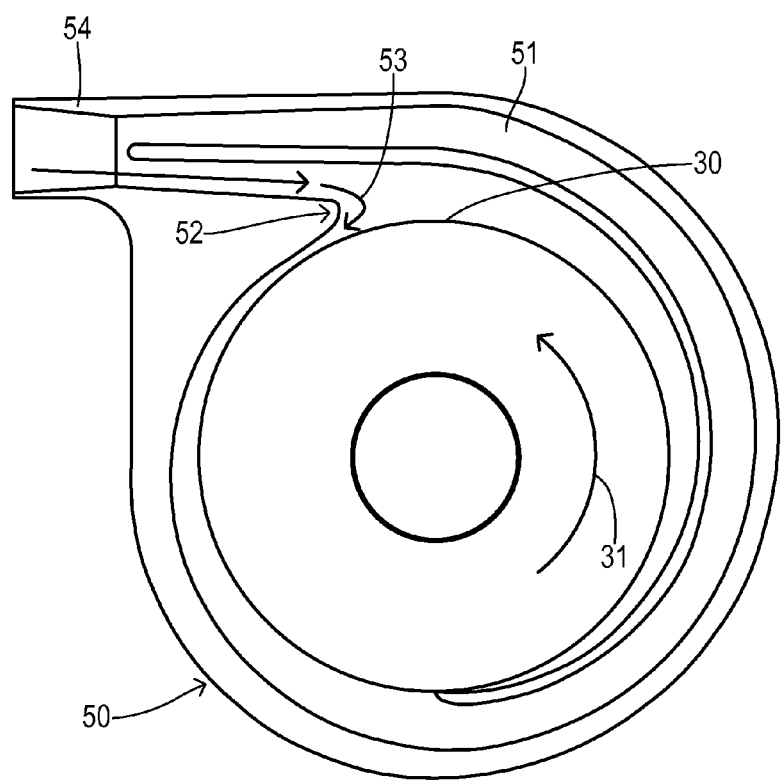
FIG. 7 is a plan view of a modified volute of the present invention.
Figure 8:
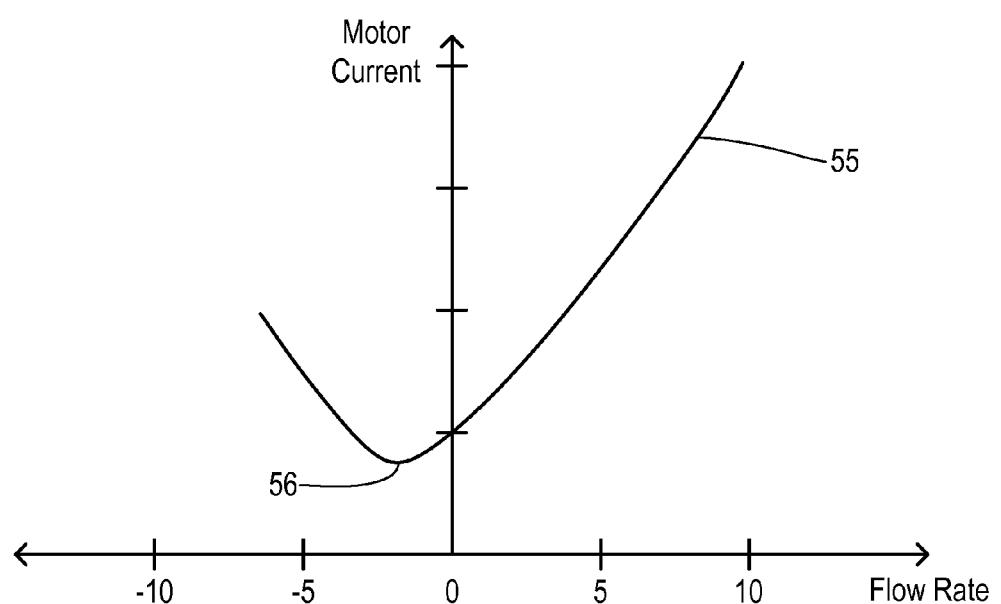
FIG. 8 is a graph showing an improved relationship between motor current and flow rate resulting from the modified volute of FIG. 7.

To overcome the foregoing difficulty, an improved pump housing 50 shown in FIG. 7 includes an outlet volute 51 including a modified separation edge 52. In particular, separation edge 52 is spaced from outer circumference 30 of the impeller in order to provide a limited backflow path 53 having a direction coinciding with pumping direction 31. Thus, a backflow of fluid is allowed to enter outlet 54 and to curve along separation edge 52 into a direction coinciding with pumping direction 31, thereby joining the impeller-driven flow and not opposing the driving force of the impeller. Although overall pump efficiency may be slightly reduced, the loss of efficiency is traded for the ability to characterize a limited range of backflow rates. A modified relation 55 is shown in FIG. 8 wherein the minima in the motor current has shifted to a flow rate less than zero. Thus, for backflow rates between zero and the minima at 56, the flow rate can be unambiguously estimated based on motor current. Relation 55 has a positive slope from a predetermined backflow rate corresponding to minima 56 up to and beyond the zero pump flow rate. As a consequence, instantaneous flow rate estimates are reliably obtained including backflow caused during pulsatile heart operation.

What is claimed is:

1. A centrifugal pump system comprising:
   a disc-shaped impeller having an outer circumference and adapted to be rotatably driven in a pumping direction;
   a housing with a pumping chamber receiving the impeller, the pumping chamber defining an outlet volute having a separation edge spaced from the outer circumference to provide a limited backflow path coinciding with the pumping direction;
   a motor for receiving a voltage and for driving the impeller in response to the voltage provided to the motor;
   a current sensor for measuring a current flow within the motor in response to the voltage; and
   a controller having a predetermined relation between the measured current and the pump flow rate, wherein the controller estimates the pump flow rate in response to said predetermined relation wherein the predetermined relation includes a positive slope from a predetermined backflow rate to a zero pump flow rate.

2. The system of claim 1 wherein the separation edge is comprised of a continuous curve.

3. The system of claim 1 wherein the housing is implantable in a patient, wherein the housing includes a central inlet for receiving blood from the patient's heart, and wherein the outlet volute is configured to be coupled to an artery of the patient so that the pump system provides a blood flow assist to the patient.

4. The system of claim 3 wherein the controller estimates a backflow resulting from pulsatile functioning of the patient's heart.

* * * * *